(12) United States Patent
Sklar et al.

(10) Patent No.: US 6,878,343 B2
(45) Date of Patent: Apr. 12, 2005

(54) DEVICES AND HOUSINGS FOR TEST SAMPLE PREPARATION

(75) Inventors: Eric R. Sklar, Northville, MI (US); Dean C. Delben, Monroe, MI (US); Daniel S. Vitkuske, Ann Arbor, MI (US)

(73) Assignee: Pall Corporation, East Hills, NY (US)

( * ) Notice: Subject to any disclaimer, the term of this patent is extended or adjusted under 35 U.S.C. 154(b) by 287 days.

(21) Appl. No.: 09/803,739

(22) Filed: Mar. 12, 2001

(65) Prior Publication Data

US 2002/0119576 A1 Aug. 29, 2002

Related U.S. Application Data

(63) Continuation of application No. 09/622,991, filed as application No. PCT/US99/04127 on Feb. 25, 1999, now abandoned.
(60) Provisional application No. 60/076,286, filed on Feb. 27, 1998.

(51) Int. Cl.$^7$ ................................................ B01L 11/00
(52) U.S. Cl. ........................ 422/101; 422/99; 422/100; 422/102; 422/104; 436/174; 436/177; 436/180; 210/473
(58) Field of Search ........................ 422/99, 100, 101, 422/102, 935, 104; 436/174, 177, 180; 210/473, 474, 477, 479

(56) References Cited

U.S. PATENT DOCUMENTS

| | | | |
|---|---|---|---|
| 4,777,021 A | * | 10/1988 | Wertz et al. ................. 422/101 |
| 4,797,259 A | * | 1/1989 | Matkovich et al. .......... 422/101 |
| 4,948,442 A | | 8/1990 | Manns |
| 4,948,564 A | * | 8/1990 | Root et al. ................... 422/101 |
| 5,141,719 A | * | 8/1992 | Fernwood et al. ........... 422/101 |
| 5,223,133 A | * | 6/1993 | Clark et al. .................. 210/232 |
| 5,264,184 A | * | 11/1993 | Aysta et al. .................. 422/101 |
| 5,342,581 A | | 8/1994 | Sanadi |
| 5,612,002 A | * | 3/1997 | Cody et al. .................. 422/131 |
| 5,846,493 A | * | 12/1998 | Bankier et al. .............. 422/101 |
| 6,054,100 A | * | 4/2000 | Stanchfield et al. ......... 422/102 |
| 6,117,394 A | * | 9/2000 | Smith .......................... 422/100 |
| 6,183,645 B1 | * | 2/2001 | DeWitt ........................ 210/634 |
| 6,267,930 B1 | * | 7/2001 | Ruediger et al. ............ 422/130 |
| 6,277,648 B1 | * | 8/2001 | Colpan ........................ 436/177 |

* cited by examiner

*Primary Examiner*—Jill Warden
*Assistant Examiner*—Dwayne K Handy
(74) *Attorney, Agent, or Firm*—Leydig, Voit & Mayer, Ltd.

(57) ABSTRACT

The description describes a test sample preparation device comprising a housing, a filter assembly disposed over an opening in the housing and including a plurality of wells, a sampler tray removably disposed in the housing, and a plurality of vials removably coupled to the sampler tray and being in liquid receiving relationship with the wells. A filter assembly is also disclosed and which comprises a cover defining an impervious wall and plurality of wells formed in the wall, each wall having first and second open ends, the second open end of the well comprising a tubular protrusion. A housing is also disclosed and comprises a generally cylindrical body, a vacuum channel providing fluid communication between the interior and the exterior of the cylindrical body, and a key mechanism including a post having first and second ends, the key mechanism being arranged to orient a sampler tray and vials with respect to the housing. A method for simultaneously preparing multiple test samples for automated liquid chromatography and a method for automated liquid chromatography are also disclosed and comprise depositing test samples into a plurality of wells, simultaneously passing the test samples through porous media disposed in the wells, and depositing the filter test samples directly into vials removably coupled to a sampler tray.

12 Claims, 7 Drawing Sheets

DEVICES AND HOUSINGS FOR TEST SAMPLE PREPARATION

This application is a continuation of U.S. application Ser. No. 09/622,991, now abandoned the United States National Phase of International Application No. PCT/US99/04127, filed Feb. 25, 1999, which claims the priority of U.S. Provisional Patent Application 60/076,286, filed Feb. 27, 1998, which application is incorporated by reference in its entirety.

TECHNICAL FIELD

The present invention relates to devices and housings for preparing test samples.

BACKGROUND OF THE INVENTION

Currently, there are a number of conventional methods for preparing multiple test samples, such as test samples for automated liquid chromatography. One of the conventional methods involves filtering and depositing a test sample into each of a number of vials using a syringe and a syringe filter contained therein. The test samples generally are sequentially filtered and deposited into the vials. The vials may be placed in a sampler tray either before or after the test samples have been deposited in the vials. Then the sampler tray and vials are placed in an automated test instrument for liquid chromatography.

Another conventional method of preparing multiple test samples involves the use of a test sample preparation device. Under this approach, the test samples are deposited into a number of wells, each of which contains a filter. A differential pressure across the filter is then applied to the test samples, and under the pressure, the test samples pass through the filters and are deposited into another set of wells. Subsequently, the filtered test samples may be transferred from the wells to a set of vials, which are then placed into a sampler tray. Next, the sampler tray and vials are placed in an automated test instrument for liquid chromatography.

Still another conventional method involves either sequentially or simultaneously filtering multiple test samples, depositing the filtered test samples into vials contained in a rack, and transferring the vials from the rack to a sampler tray.

There are a number of disadvantages associated with the conventional methods of preparing multiple test samples. For example, it is time-consuming to sequentially filter test samples and deposit them into vials, to transfer filtered test samples from wells to vials, or to transfer vials from a rack to a sampler tray. Additionally, sample losses occur when test samples are transferred from wells to vials. Further, there is a risk of contamination during the transfer of test samples from wells to vials and during the transfer of vials from a rack to a sampler tray.

SUMMARY OF THE INVENTION

According to one aspect of the invention, a test sample preparation device may comprise a housing, a filter assembly, a sampler tray, an plurality of vials, and a key mechanism. The housing may have an opening, an interior, and exterior, and a vacuum channel. The vacuum channel provides fluid communication between the interior and exterior of the housing and is capable of coupling a vacuum source to the interior of the housing. The filter assembly is disposed over the opening of the housing and includes a plurality of wells. Each well has two open ends. The filter assembly also includes a plurality of porous media that are respectively disposed in the wells. The sampler tray is removably disposed in the housing, and the plurality of vials are removably disposed in the sampler tray in liquid receiving relationship with the wells, respectively. The key mechanism is coupled to the housing. The housing and the sampler tray have a generally cylindrical configuration. and the key mechanism uniquely defines the circumferential position of the vials in the housing.

According to another aspect of the invention, a test sample preparation device, which may be used for simultaneously preparing multiple samples directly into vials coupled to a sampler tray, may comprise a housing, a filter assembly, a sampler tray and a plurality of vials. The housing may have an opening, an interior and an exterior, and a vacuum channel. The vacuum channel provides fluid communication between the interior and the exterior of the housing and is capable of coupling a vacuum source to the interior of the housing. The filter assembly is disposed over the opening of the housing and includes a plurality of wells each having two open ends and a plurality of porous media that are disposed in the wells, respectively. The sampler tray is removably disposed in the housing. The plurality of vials are removable coupled to the sampler tray and are in liquid receiving relationship with the wells, respectively. The test sample preparation device may further comprise a key mechanism coupled between the sampler tray and the housing to uniquely define the position of each vial with respect to the housing.

According to another aspect of the invention, a test sample preparation device may comprise a housing, a filter assembly, a sampler tray, an plurality of vials, and a key mechanism. The housing may have an opening, an interior, an exterior, and a vacuum channel. The vacuum channel provides fluid communication between the interior and exterior of the housing and is capable of coupling a vacuum source to the interior of the housing. The filter assembly is disposed over the opening of the housing and includes a plurality of wells. Each well has two open ends. The filter assembly also includes a plurality of porous media that are respectively disposed in the wells. The sampler tray is removably disposed in the housing, and the plurality of vials are removably disposed in the sampler tray in liquid receiving relationship with the wells, respectively. The key mechanism is coupled to the housing to uniquely define the position of each vial with respect to the housing. The key mechanism includes a post having a first and second ends, an annular protrusion at the second end of the post, and a notch in the annular protrusion.

According to another aspect of the invention, a housing which holds a sampler tray containing vials receiving a liquid sample may comprise a generally cylindrical body that includes open and closed ends and has an interior and an exterior, a vacuum channel that provides fluid communication between the interior of the cylindrical body and the exterior of the cylindrical body, and a key mechanism. The key mechanism includes a post that has first and second ends with the first end being attached to the closed end of the cylindrical body, an annular protrusion disposed at the second end of the post, and a notch disposed within the annular protrusion. The key mechanism is arranged to orient the sampler tray and the vials with respect to the housing.

For some embodiments of the invention, the filter assembly may be used for simultaneously preparing multiple samples directly into vials and may comprise a cover defining an impervious wall with the plurality of wells unitarily formed in the wall. The first and second open ends of each well define a fluid flow path through the wall of the cover via the well between the first end of the well and the second end of the well, wherein each well includes a support and the porous medium is mounted to the support. The support extends across the fluid flow path of the well and contacts the porous medium whereby fluid flowing through the well from the first end of the well to the second end of the well flows through the porous medium and past the support. The first end of the well is upstream of the porous medium and the second end of the well is downstream of the porous medium, wherein the second end of the well comprises a tubular protrusion which, when a vial is placed in liquid receiving relationship with the well, is capable of extending into the vial to minimize cross-contamination.

Some embodiments of the invention may be used in a method for simultaneously preparing multiple test samples for automated liquid, chromatography, the method comprising depositing test samples into the plurality of wells, simultaneously passing the test sample through the porous media disposed in the wells, and depositing the filtered test samples directly into the vials removably coupled to the sampler tray.

Some embodiments of the invention may be used in a method for automated liquid chromatography, the method depositing test samples into the plurality of wells, simultaneously passing the test samples through the porous media disposed in the wells, depositing the filtered test samples directly into the vials removably coupled to a sampler tray, and directing the filtered test samples contained in the vials removably coupled to the sampler tray through an automated liquid chromatography device.

DETAILED DESCRIPTION OF THE EMBODIMENTS

Figure 1:
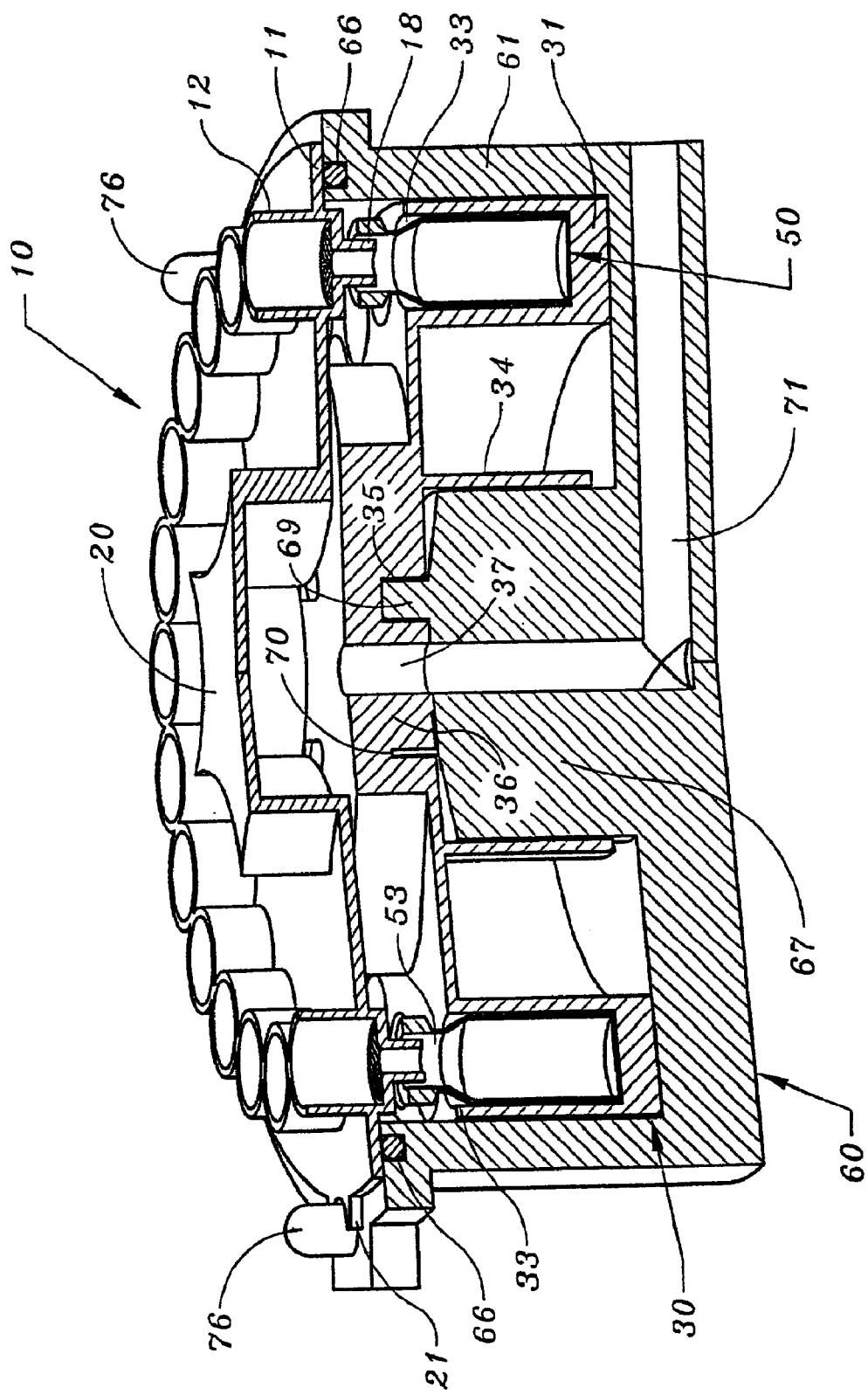
FIG. 1 is a schematic cross-sectional view of a test sample preparation device embodying the present invention.
Figure 2:
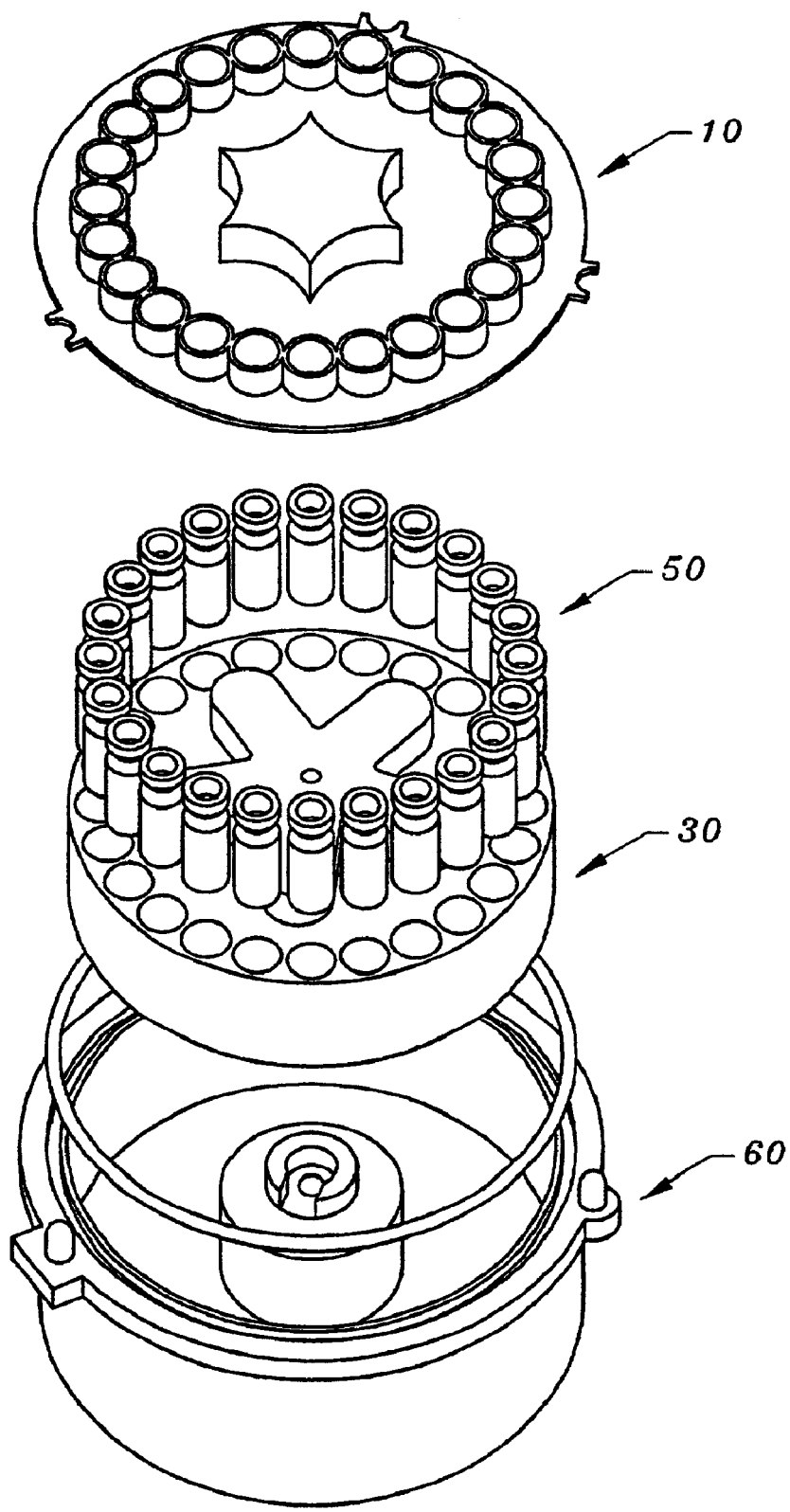
FIG. 2 is an exploded view of the embodiment of the invention shown in FIG. 1.

As shown in FIGS. 1 and 2, an exemplary test sample preparation device comprises a housing 60, a filter assembly 10, a sampler tray 30, a plurality of vials 50 and a key mechanism 21. The filter assembly 10 may include a plurality of wells 12, each of which contains a microporous filter 13 (FIG. 3a) or any suitable porous medium, such as a solid phase extraction medium. The vials 50 may be removably coupled to the sampler tray 30, and the sampler tray 30 and the vials 50 may be removably disposed in the housing 60. The filter assembly 10 may be removably connected to the housing 60, and the vials 50 preferably are in liquid receiving relationship with the wells 12, respectively. By applying a vacuum to the housing 60, test samples contained in the wells 12 may be passed through the filters 13 and deposited directly into the vials 50 in the sampler tray 30. The vials 50 and the sampler tray 30 may then be removed from the housing 60 and placed, for example, in an automated instrument for liquid chromatography.

The filter assembly may have any suitable configuration that supports the plurality of microporous filters and allows the test samples to pass through the microporous filters and into the vials in the sampler tray. The filter assembly may comprise a cover that defines an impervious wall, a plurality of wells that are preferably formed in the wall, and a plurality of microporous filters disposed respectively in the wells. Preferably, the cover and the wells have a unitary construction to enhance the strength of the filter assembly. Each well may have first and second open ends that define a fluid flow path through the wall of the cover, and may include a filter support to which the microporous filter contained in the well is mounted. The filter support extends across the fluid flow path of the well whereby a liquid test sample flows through the microporous filter and passes through the filter support. Accordingly, the filter support may also provide drainage to the microporous filter in addition to support. Further, the filter may be sealed to the filter support to prevent the test sample from bypassing the filter. Alternatively, the filter may be sealed to the inner wall of the well for the same purpose. The second end of the well may include a tubular protrusion which, when a vial is placed in liquid receiving relationship with the well, is capable of extending to or into the vial to minimize cross-contamination. Cross-contamination as used herein is defined as the migration of test sample from one vial to an adjacent vial. Obviously, cross-contamination may lead to spurious test results.

The cover may be variously configured. For example, the cover may be generally circular or polygonal, and it may have a generally flat configuration, a partially spherical configuration, or a generally cylindrical configuration with a first end comprising the imperious wall and an opposite open or closed end.

The wells may also have any one of various configurations, such as a polygonal, cylindrical or conical configuration, or a combination thereof, although the wells preferably have a cylindrical configuration. The wells may have generally the same size and shape, or different sizes and/or shapes. For example, the wells may have the same cylindrical configuration but different diameters and/or heights. Because the wells may be used to receive and contain test samples, the size of each well may be determined by the volume of the test sample to be deposited in the well. It may be desirable for the wells to include an arrangement for receiving a test sample delivery device, such as a syringe or a pipette. There may be any number of wells disposed in the wall of the cover, and they may be arranged in a number of configurations. For example, any number of wells may be arranged in a row or a plurality of rows, or they may be arranged in a circle or a plurality of concentric circles. However, the number and arrangement of the wells may be dictated by the number and arrangement of the vials in the sampler tray because the vials are preferably in one-to-one liquid receiving relationship with the wells.

The filter support may be of any suitable configuration that provides support and/or drainage to the filter. Preferably, when the filter is mounted to the filter support, a seal is provided that prevents the test sample from bypassing the filter. The filter support may be unitarily or integrally formed with the well, or it may be a separate part disposed in the well.

The filters are preferably microporous filters, which may be any suitable type of filter, such as a fibrous type or a membrane type. In some embodiments of the filter assembly, the wells may contain different types of microporous filters, depending on the requirements of sample preparation. The microporous filters may be used to filter any particulates or colloidal particles, including, for example, gross contaminants and insolubles. Although a microporous filter is typically used with the present invention, the wells may contain porous media of any other type, such as porous media for solid phase extraction (SPE).

The key mechanism may be of any configuration that orients the wells of the filter assembly with respect to the vials contained in the housing. Preferably, the key mechanism allows each well to be uniquely aligned with the housing and/or with a particular vial. This feature is especially useful when the wells contain different types of test samples, and, therefore, each well and/or vial preferably can be individually identified.

Figure 3A:
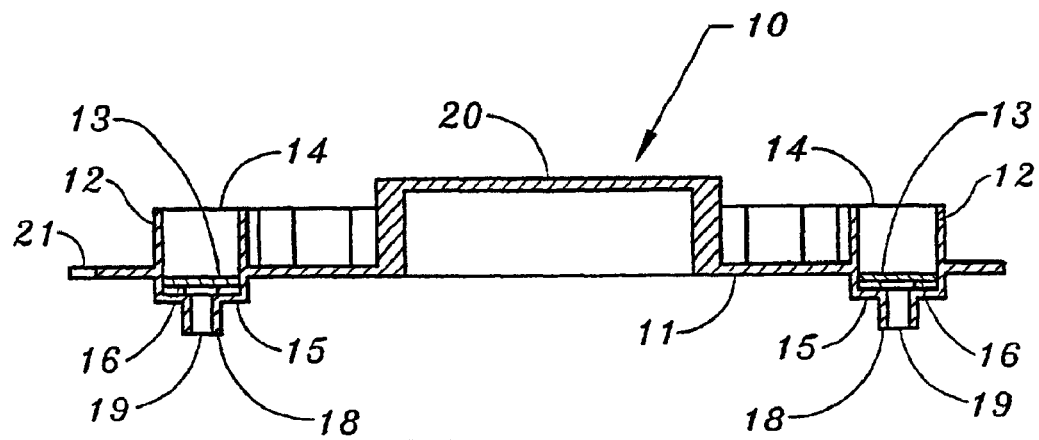
FIG. 3a is a schematic cross-sectional view of the filter assembly shown in FIG. 2.

An exemplary embodiment of the filter assembly is shown in FIG. 3a. The filter assembly 10 may comprise a circular cover plate 11 defining an impervious wall, a plurality of cylindrical wells 12 integrally or unitarily formed in the cover plate 11, and a plurality of circular microporous filters 13, one of which is disposed within each well 12. In this embodiment, there are twenty-four wells 12 of the same diameter and height, which are arranged in a single circle near the outer periphery of the cover plate 11. Preferably, the diameter of the circle is substantially equal to the diameter of the circle in which the vials are arranged, so that the vials may be placed in fluid receiving relationship with the wells 12. Each well 12 has first and second open ends 14, 15 that define a fluid flow path through the wall of the cover plate 11. The cover plate 11 may intersect the wells 12 at either end 14, 15 of the wells 12, or it may intersect the wells 12 anywhere between the two ends 14, 15 of the wells 12.

In the embodiment shown in FIG. 3a, the second end 15 of the well 12 may include a filter support 16 to which the microporous filter 13 is mounted. Alternatively, the filter support 16 may be disposed at the first end 14 of the well 12 or between the first and second ends 14, 15. However, to reduce hold-up volume, the filter support 16 is preferably disposed at or near the second end 15 of the well 12. The filter support may be any arrangement which provides the microporous filter 13 with support and drainage. For example, the filter support 16 may comprise a plurality of protrusions, such as bumps, that provide support and drainage for the microporous filter. The filter support may be unitarily or integrally formed within the well 12 at the second end 15, or it may be a separate part disposed at the second end 15 preferably within the well 12.

Figure 3B:
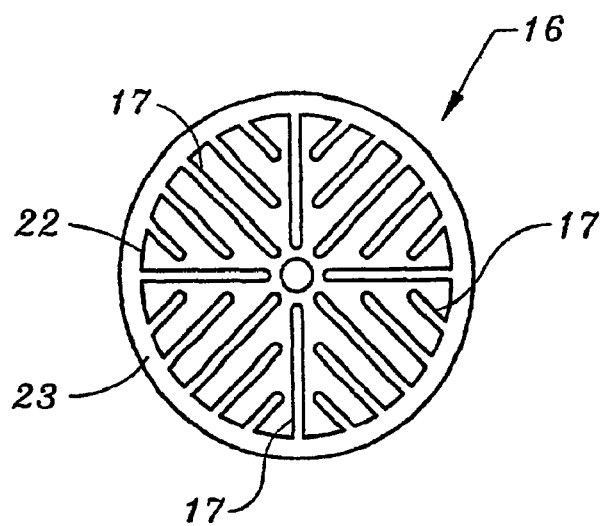
FIG. 3b is a top view of the filter support.

As shown in FIG. 3b, a preferred embodiment of the filter support 16 may include a circular depression 22 and a plurality of ribs 17 formed within the circular depression 22. The filter 13, preferably circular, may be mounted to the filter support 16 in a number of ways. For example, the filter 13 may be simply laid over the filter support 16, or it may be bonded to the filter support 16 by means of, for example, thermal welding or adhesive. If the filter 13 is bonded to the filter support 16, the filter 13 preferably is bonded to both the ribs 17 and an annular area 23 between the sidewall of the well 12 and the circular depression 22. Accordingly, the bond between the filter 13 and the annular area 23 preferably provides a seal that prevents the test sample from bypassing the filter 13; the ribs 17 preferably provide support to the filter 13; and the grooves between the ribs 17 preferably provide drainage to the filter 13.

The second end 15 of the well 12 also includes a tubular protrusion 18 extending away from the well 12. The opening at the second open end 15 includes an aperture 19 that extends through the second open end 15 and through the tubular protrusion 18. When a vial 50 is placed in liquid receiving relationship with the well 12, the tubular protrusion 18 has an outer diameter and length which substantially reduces or eliminates the possibility of sample cross-contamination. For example, the tubular protrusion 18 may extend to or even into the opening 51 of the vial 50 to minimize cross-contamination. In addition, when the vial 50 is placed in fluid receiving relationship with the well 12, the protrusion 18 preferably does not substantially close the opening 53 of the vial 50. Preferably the gap between the protrusion 18 and the vial 50 is sufficiently large such that the liquid in a vial 50 is not eluted from the vial 50 when a vacuum is applied to the interior of the housing 60 (and the exterior of the vial 50). Elution occurs when the liquid in a vial is expelled by the air exiting the vial under a vacuum applied to the exterior of the vial. A large gap between the protrusion 18 and the vial 50 may prevent or reduce elution. Similarly, the gap between the bottom 15 of the well 12 and the top of the vial 50 preferably is sufficiently large to prevent or reduce elution.

The key mechanism 21 of the filter assembly 10 may comprise three notches 21 that are capable of engaging the three pins 76 of the housing 60 to orient the filter assembly 10 and the wells 12 with respect to the housing 60 and/or the vials 50. The functions of the key mechanism 21 are described subsequently in connection with the discussion on the alignment of the wells 12 and the vials 50.

Additionally, the cover plate 11 may include a handle or a protrusion, such as the protrusion 20 at the center of the cover plate 11 shown in FIG. 3a, which allows the cover plate 11 to be conveniently lifted by hand or by a lifting device.

The test sample preparation device of the present invention may be used in a wide variety of applications. For example, the sampler tray may be a sampler tray designed as a part of an automated liquid chromatography instruments, and the test sample preparation device is then designed to include and accommodate the sampler tray. The sampler tray may be of any configuration that a designer of chromatography instruments chooses. It may have a generally cylindrical or parallelepipedal configuration, or any other configuration that allows vials to be conveniently placed in and removed from the sampler tray. The vials may be arranged in the sampler tray in any manner that a designer of chromatography instrument may choose. For example, the vials may be arranged in a row or rows, or a circle or several concentric circles. The vials usually have a cylindrical configuration with an open end and a closed end, although they may have any configuration that can hold a test sample. The vials may have the same configuration and size, or they may have different configurations and/or sizes. The size of a vial may be determined by the volume of the test sample to be contained in the vial.

Figure 4:
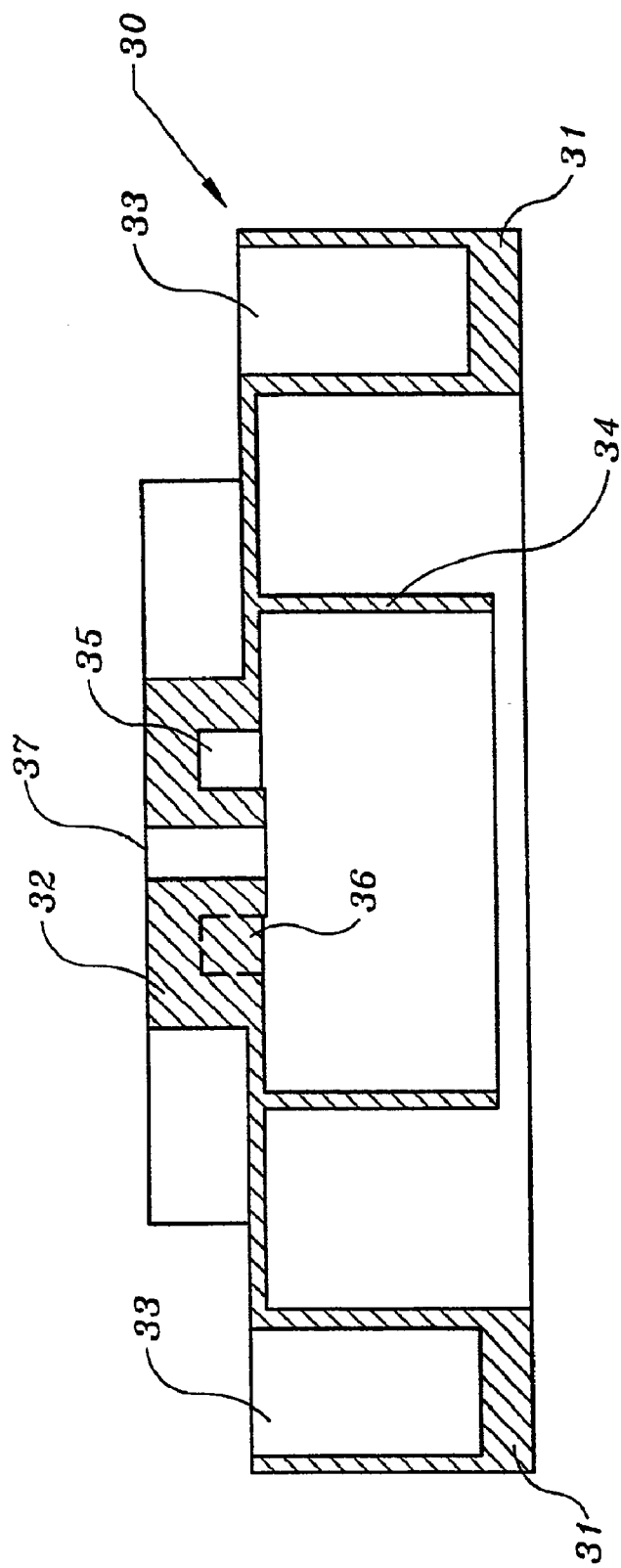
FIG. 4 is a schematic cross-sectional view of the sampler tray shown in FIG. 2.
Figure 5:
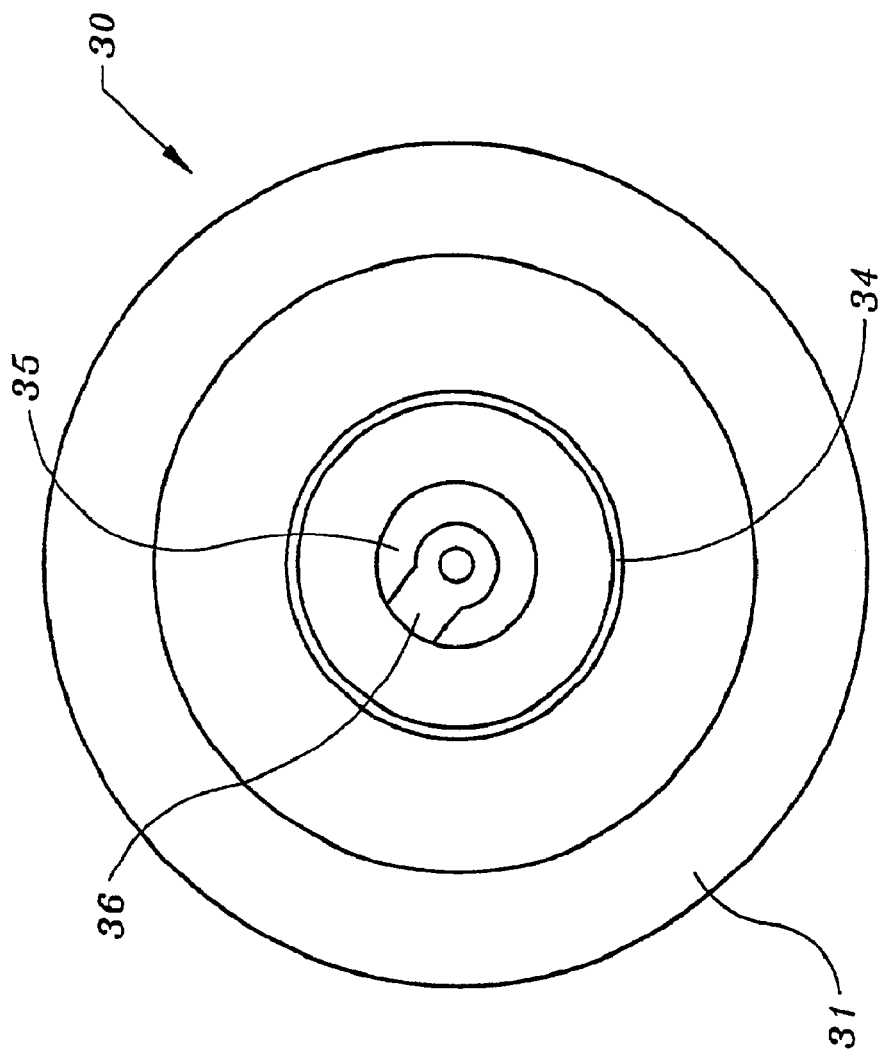
FIG. 5 is a bottom view of the sampler tray shown in FIG. 2.

An exemplary embodiment of a sampler tray is shown in FIGS. 4 and 5. The exemplary embodiment 30 comprises a cylindrical sidewall 31 and a circular plate 32 attached to an end of the cylindrical sidewall 31. There may be a total of, for example, 24 blind cylindrical bores 33 for receiving vials 50, the bores 33 being arranged in a circle along the outer periphery of the circular plate 32. The bores 33 extend through the plate 32 and into, but not through, the cylindrical sidewall 31. The sampler tray 30 also includes a cylindrical sleeve 34, an end of which is attached to the plate 32. The cylindrical sleeve may be in concentric relationship with the cylindrical sidewall 31. The portion of the plate 32 within the cylindrical sleeve 34 includes an annular groove 35 concentrically arranged with the cylindrical sleeve 34 and with the cylindrical sidewall 31. Within the annular groove 35, there is a radially oriented ridge 36 extending across the groove 35. At the center of the plate 32 and within the annular groove 35, there is an aperture 37 extending through the plate 32.

Figure 6:
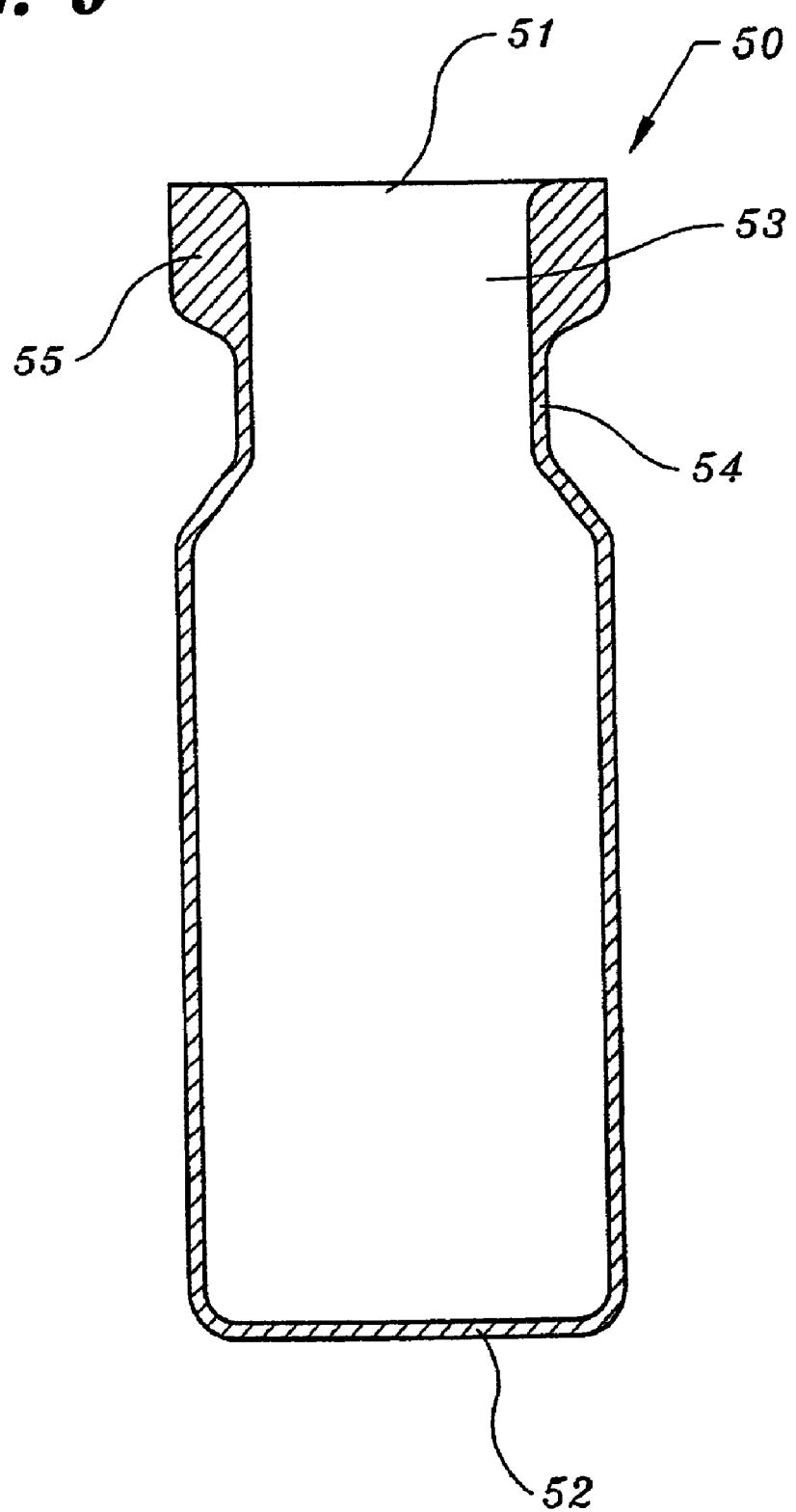
FIG. 6 is a schematic cross-sectional view of one of the vials shown in FIG. 2.

Shown in FIG. 6 is an exemplary embodiment of a vial 50. The vial 50 has a configuration similar to that of a bottle, i.e., a cylindrical, hollow configuration with an open end 51 and a closed end 52, and a narrow opening 53 and a narrow neck 54 at its open end 51. There is also outwardly extending radial flange 55 at the open end 51 of the vial 50.

The housing may be variously configured. For example, it may have a generally parallelepipedal or cylindrical configuration and may include a sidewall, an open end and a closed end. The cover of the filter assembly may be disposed over the open end of the housing. If a vacuum channel is included in the housing, it may be placed anywhere in the housing, such as on the sidewall and/or the closed end. The housing may also include an arrangement that orients the filter assembly and/or the sampler tray with respect to the housing, and that allows the vials to be placed in fluid receiving relationship with the wells of the filter assembly, respectively. This arrangement may also relate specific wells to specific vials. While this arrangement preferably associates the housing with the filter assembly and/or the sampler tray, it may directly associate the filter assembly with the sampler tray.

The arrangement may include a key mechanism for orienting the filter assembly with respect to the housing and/or another key mechanism for orienting the sampler tray with respect to the housing. Preferably, the key mechanism for orienting the filter assembly uniquely defines the position of each well with respect to the housing, and the key mechanism for orienting the sampler tray uniquely defines the position of each vial with respect to the housing. Thus, the two key mechanisms may be arranged so that each well can only be placed in fluid receiving relationship with a particular vial and with no other vials.

A mechanism for applying a differential pressure across the filters may be coupled to the filter assembly to facilitate the passing of the test samples through the filters. The differential pressure may be applied to all of the wells to simultaneously pass samples through the wells, or the differential pressure may be applied multiple times to one or more of the wells to pass samples through the wells sequentially. Any suitable mechanism may be used for applying such a differential pressure, including, for example, a gas pressure source placed over one or more of the wells to force the sample in the well through the filter and into the vial. Preferably, the mechanism may include a vacuum source which may be coupled to the filter assembly or preferably to the housing. For example, the vacuum source may be coupled to the housing and communicate with the interior of the housing. The vacuum source may be any device, such as a pump, that provides a pressure less than the atmosphere pressure. For example, a pump may be arranged with the housing to have its suction port in fluid communication with the interior of the housing and its pressure port in fluid communication with the exterior of the housing. The vacuum source may be an integral part of the housing and may be disposed within or without the housing. Alternatively, the vacuum source may be a part separate from the housing, such as a pump disposed outside of the housing and having its suction port directly or indirectly connected to a vacuum channel in the housing, for example, via a tube or the like. Alternatively, the cover instead of the housing may include such a vacuum channel, and a vacuum source may be similarly coupled to the vacuum channel. The vacuum source may be powered by any power source such as an electric motor.

Figure 7:
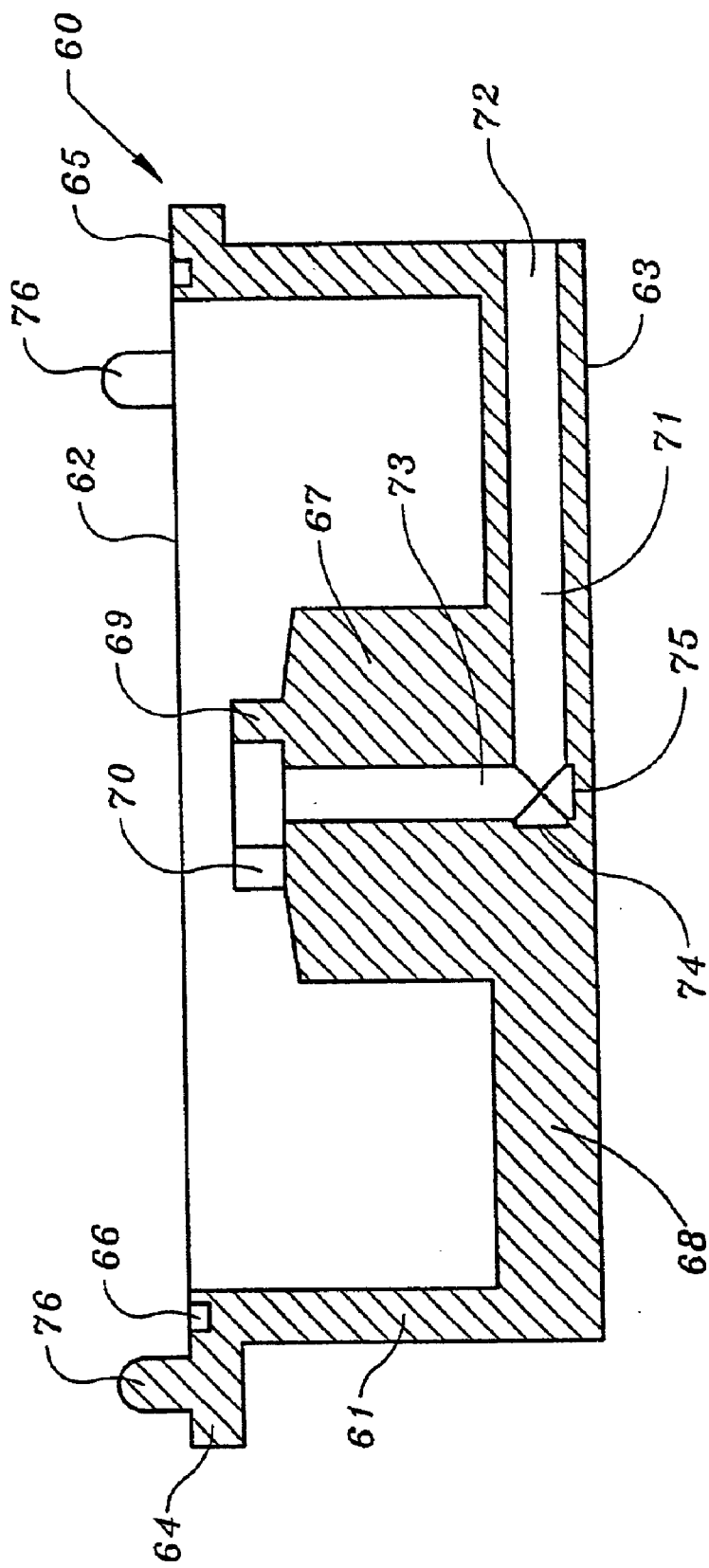
FIG. 7 is a schematic cross-sectional view of the housing shown in FIG. 2.

As shown in FIG. 7, an exemplary embodiment 60 of the housing may include a cylindrical sidewall 61 with an open end 62 and a closed end 63. The cover plate 11 of the filter assembly 10 may be disposed over the open end 62 to enclose the housing 60. There may be an outwardly extending radial flange 64 at the open end 62 of the cylindrical sidewall 61. The flange surface 66 facing the cover plate 11 preferably includes an annular groove 65, and a pliable gasket 66 or an O-ring seal may be disposed in the groove 65 to provide an airtight seal between the housing 60 and the filter assembly 10. Alternatively, a groove may be placed in the cover of the filter assembly and a seal may be disposed in the groove to provide an airtight seal between the housing and the filter assembly.

A cylindrical post 67 may be disposed in the housing 60, one end of the cylindrical post 67 being attached to the interior surface of the closed end wall 68 of the housing 66. On the unattached end of the cylindrical post 67, there may be an annular protrusion 69 which is preferably concentrically arranged with the cylindrical post 67, and the annular protrusion 69 may include a notch 70.

In this embodiment, the housing 60 includes a vacuum channel 71, which comprises first and second blind apertures 72, 73 that intersect at their blind ends 74, 75. The first aperture 72 is disposed within the closed end wall 68 and extends radially from the center of the closed end wall 68 to the side wall 61. The second aperture 73 is disposed at the center of the cylindrical post 67 and extends from the unattached end of the cylindrical post 67 to the center of the closed end wall 68 and intersects the blind end 74 of the first aperture 72. Thus, the vacuum channel 71 and the aperture 37 of the sampler tray 30 provide fluid communication between the interior and the exterior of the housing 60. A vacuum source (not shown) may be directly coupled to the vacuum channel 71, or it may be indirectly coupled to the vacuum channel 71 through a tube or the like (not shown). A nipple fitting (not shown) or the like may be installed at the opening of the vacuum channel 71, i.e., the open end of the aperture 72, to facilitate the coupling of the vacuum source to the vacuum channel 71.

When a vacuum is applied to the interior of the housing 60, the center portion of the filter assembly 10 may deflect downwardly under the atmosphere pressure and partially block the aperture 37 and the vacuum channel 71. Thus, the filter assembly preferably has sufficient strength or is configured to prevent the blockage of the aperture 37 and the vacuum channel 71.

When the filter assembly is disposed over the opening of the housing and the sampler tray and the vials contained therein are disposed in the housing, the vials are preferably placed in fluid receiving relationship with the wells. This may entail that each well is substantially coaxially arranged with a vial and the tubular protrusion of the well extends to or into the opening of the vial. More preferably, each well can only be placed in fluid receiving relationship with a particular vial and with no other vials. There are many different ways to accomplish this. With respect to the embodiment shown in FIG. 1, for example, this can be accomplished by concentrically arranging the sampler tray 30 with the filter assembly 10, uniquely aligning circumferentially the vials 50 with the wells 12 and setting the axial distance between the vials 50 and the wells 12. In this embodiment, the desired spatial relationship between the wells 50 and the vials 12 are indirectly defined by defining the spatial relationship between the sampler tray 30 and the housing 60 and the spatial relationship between the filter assembly 10 and the housing 60.

As shown in FIGS. 1, 2, 4, 5 and 7, the spatial relationship between the sampler tray 30 and the housing 60 may be defined, for example, by the location of the cylindrical post 67, the location of the notch 70 and the height of the sidewall 61 of the housing 60. When the sampler tray 30 and the vials 50 contained therein are placed in the housing 60, the cylindrical sleeve 34 of the sampler tray 30 is preferably disposed adjacent to the outer periphery of the cylindrical post 67. Preferably, the inner diameter of the cylindrical sleeve 34 is substantially equal to but slight more than the diameter of the cylindrical post 67. This aligns the center of the sampler tray 30 and the center of the housing 60, and places the sampler tray 30 and the housing 60 in concentric relationship. The annular protrusion 69 of the housing 60 is preferably disposed within the annular groove 35 of the sampler tray 30, and the ridge 36 is preferably disposed within the notch 70. This uniquely defines the circumferential positions of the vials 12 relative to the housing 60. In addition, the open end of the cylindrical sidewall 31 contacts the inner surface of the closed end wall 68 of the housing 60, and, therefore, the height of the sidewall 61 of the housing 60 may be chosen to define the axial positions of the vials 50 relative to the housing 60. Accordingly, the key mechanism for orienting the sampler tray 30 and the vials 50 with respect to the housing 60 may include one or more of the cylindrical post 67, the annular protrusion 69, the notch 70 and the side wall 61.

As shown in FIGS. 1, 2, 3a and 7, the spatial relationship between the filter assembly 10 and the housing 60 may be defined by the three pins 76 and the three notches 21, although four or more pins and notches may be used. Preferably the three pins 76 are arranged in a circle and are perpendicularly attached to the flange surface 65 facing the cover plate 11. The three notches 21 may be located along the outer periphery of the cover plate 11. When the filter assembly 10 is disposed over the opening 62 of the housing 60, the three notches 21 engage the three pins 76 to align the filter assembly 10 with the housing 60. If the three notches 21 and three pins 76 are equally spaced circumferentially, each notch 21 may engage any one of the three pins 76, and accordingly, each well 12 may be in one of three possible positions relative to the housing 60. If the three notches 21 and three pins 76 are not equally spaced circumferentially, each notch 21 will always engage the same pin 76, and accordingly, each well 12 will only be in same circumferential position relative to the housing 60, thereby uniquely identifying each well with a particular vial. Accordingly, the key mechanism for orienting the filter assembly 10 and the wells 12 with respect to the housing 60 may include the three pins 76 and their locations. Additionally, the axial positions of the wells 12 may be defined by adjusting the location on the well 12, at which the cover plate 11 intersects the wells 12. The cover plate 11 may intersect the wells 12 at either end 14, 15 of the wells 12, or it may intersect the wells 12 anywhere between the two ends 14, 15.

Consequently, the sampler tray 30 and the filter assembly 10 may be concentrically arranged by adjusting either the position of the cylindrical post 67 or the positions of the three pins 76, or both. The vials 50 and the wells 12 may be circumferentially aligned by adjusting either the position of the notch 70 or the positions of the three pins 76, or both. If the positions of the three pins 76 are not equally spaced circumferentially, each vial 50 is uniquely aligned with a specific well 12. The axial relationship between the vials 50 and the wells 12 can be arranged by adjusting either the height of the sidewall 61 of the housing 60, the location on the wells 12, at which the cover plate 11 intersects the wells 12, or the length of the tubular protrusions 18 at the second ends 15 of the wells 12.

Other arrangements for aligning the wells and vials may be used in place of the one described above. For example, the filter assembly may be keyed directly to the sampler tray to ensure that the vials are in proper fluid receiving relationship with the wells.

The filter assembly (except the porous media), the sampler tray, the vials, and the housing may be made from any suitable materials that provide sufficient strength and chemical resistance. Preferred materials are stainless steel and thermoplastic resins including polyolefins, such as polypropylene and polystyrene.

Embodiments of the invention may be used in a variety of applications including, for example, particulate filtration or solid phase extraction. If the embodiment shown in FIG. 1 is used for particulate filtration, the sampler tray 30 and the vials 50 contained therein may be placed in the housing 60, and the vials 50 may be placed in fluid receiving relationship with the wells 12 of the filter assembly 10. Test samples may then be deposited in the wells 12 of the filter assembly 11, either sequentially or simultaneously. The test samples may be of the same kind or of different kinds, depending on the kinds of tests to be conducted. During or after the placement of the test samples into the wells, a vacuum source may apply a vacuum to the interior of the housing 60, which creates a differential pressure across the filters 13 disposed in the wells 12. The vacuum inside the housing 60 draws the test samples through the filters 13, and the filtered test samples are then deposited into the vials 50 in the sampler tray 30. The filters 13 may be of the same kind or of different kinds, depending on the kinds of sample preparation desired. The vacuum inside the housing 60 also draws the cover plate 11 towards the flange 64 of the housing 60 and compresses the pliable gasket 66, providing an airtight seal between the filter assembly 10 and the housing 60. Subsequently, the vacuum is removed, the filter assembly 10 is removed, and then the sampler tray 30 and the vials 50 contained therein are removed from the housing 60. The sampler tray 30 and the vials 50 contained therein are then placed in an automated liquid chromatography instrument. The sampler of the instrument may select one or more of the test samples contained in the vials for processing.

If the embodiment shown in FIG. 1 is used for solid phase extraction, a waste tray (not shown) may be first placed in the housing 60. Samples containing liquid and solids may then be deposited in the wells 12 of the filter assembly 11 above a solid phase extraction medium. During or after the placement of the samples into the wells 12, a vacuum source may apply a vacuum to the interior of the housing 60, and the vacuum draws the samples through the SPE porous media (not shown) contained in the wells 12. The solids are retained by the SPE porous media as the samples pass through the SPE porous media, and the waste liquid is deposited into the waste bowl. Subsequently, the waste bowl is removed from the housing 60, and the sampler tray 30 and the vials 50 contained therein may be placed in the housing 60 with the vials 50 in fluid receiving relationship with the wells 12 of the filter assembly 10. Eluant may then be deposited in the wells 12 of the filter assembly 11. A vacuum source may apply a vacuum to the interior of the housing 60, and the vacuum draws the eluant through the SPE porous media. The eluate is then deposited into the vials 50 in the sampler tray 30. Subsequently, the sampler tray 30 and the vials 50 contained therein are removed from the housing 60, and are then placed in an automated liquid chromatography instrument. The sampler of the instrument may then select one or more of the test samples contained in the vials for processing.

A method for preparing multiple test samples may comprise depositing test samples into a plurality of wells, passing the test samples through filters deposited in the wells and depositing the filtered test samples directly into vials removably coupled to a sampler tray. The test samples may be deposited into the wells in many different ways. For example, a whole test sample may be deposited into a well once, or it may be deposited into a well in multiple steps, and in each step, a different component of the test sample may be deposited into the well. The test samples may be deposited in the wells, either sequentially or simultaneously, or some of the test samples may be deposited in the wells sequentially while others may be deposited in the wells simultaneously. The passing of the test samples through the filters may also be accomplished in a variety of ways. For example, a single application of the differential pressure across the filters may be utilized to facilitate the simultaneous passing of the test samples through the filters. Alternatively multiple applications of the differential pressure may be used to facilitate the sequential passing of test samples through the filters.

The method may include additional steps. For example, before test samples are deposited into the wells, the sampler tray and the vials contained therein may be placed in a housing of a test sample preparation device. A cover of a filter assembly may be placed over an opening of the housing and may enclose the housing. Preferably the vials are placed in liquid receiving relationship with the wells of the filter assembly. After the filtered test samples are deposited directly into the vials, the sampler tray and the vials contained therein may be removed from the housing and placed in an automated liquid chromatography device. An auto sampler of the automated liquid chromatography device may then select one or more of the test samples contained in the vials for liquid chromatography.

The ornamental aspects of the filter assembly and/or the housing as shown and/or described herein are also an aspect of the invention.

While the invention has been described in terms of several embodiments, it is not limited to those embodiments. Rather, the invention encompasses all modifications, equivalents, and alternatives that are within the spirit and scope of the following claims.

We claim:

1. A test sample preparation device for simultaneously preparing multiple samples directly into vials coupled to a sampler tray, the device comprising:

a housing having an opening, an interior and an exterior, the housing including a vacuum channel, the vacuum channel providing fluid communication between the interior and the exterior of the housing and being capable of coupling a vacuum source to the interior of the housing;

a filter assembly disposed over the opening of the housing, the filter assembly including a plurality of wells, each well having two open ends, and a plurality of porous media disposed in the wells, respectively;

a sampler tray removably disposed in the housing;

a plurality of vials removably coupled to the sampler tray, the vials being in liquid receiving relationship with the wells, respectively, and a key mechanism coupled to the housing, wherein the housing and the sampler tray each have a generally cylindrical configuration and the key mechanism uniquely defines the circumferential position of the vials in the housing.

2. The test sample preparation device of claim 1 wherein the filter assembly includes a cover defining an impervious wall and the plurality of wells are unitarily formed in the wall, wherein the first and second open ends of each well define a fluid flow path through the wall of the cover via the well between the first end of the well and the second end of the well, wherein each well includes a support and the porous medium is mounted to the support, the support extending across the fluid flow path of the well and contacting the porous medium whereby fluid flowing through the well from the first end of the well to the second end of the well flows through the porous medium and past the support, the first end of the well being upstream of the porous medium and the second end of the well being downstream of the porous medium, and wherein the second end of the well comprises a tubular protrusion which, when a vial is placed in liquid receiving relationship with the well, is capable of extending into the vial to minimize cross-contamination.

3. A housing which holds a sampler tray containing vials for receiving a liquid sample, the housing comprising:

a generally cylindrical body including open and closed ends and having an interior and an exterior;

a vacuum channel providing fluid communication between the interior of the cylindrical body and the exterior of the cylindrical body; and a key mechanism including a post having first and second ends, the first end of the post being attached to the closed end of the cylindrical body, an annular protrusion disposed at the second end of the post, and a notch disposed within the annular protrusion, wherein the key mechanism is arranged to orient the sampler tray and the vials with respect to the housing.

4. A test sample preparation device for simultaneously preparing multiple samples directly into vials coupled to a sampler tray, the device comprising:

a housing having an opening, an interior and an exterior, the housing including a vacuum channel, the vacuum channel providing fluid communication between the interior and the exterior of the housing and being capable of coupling a vacuum source to the interior of the housing;

a filter assembly disposed over the opening of the housing, the filter assembly including a plurality of wells, each well having two open ends, and a plurality of porous media disposed in the wells, respectively;

a sampler tray removably disposed in the housing;

a plurality of vials removably coupled to the sampler tray, the vials being in liquid receiving relationship with the wells, respectively; and a key mechanism coupled between the sampler tray and the housing to uniquely define the position of each vial with respect to the housing.

5. The test sample preparation device of claim 4 wherein the housing and the sampler tray each have a generally cylindrical configuration and the key mechanism uniquely defines the circumferential position of the vials in the housing.

6. The test sample preparation device of claim 5 wherein the key mechanism comprises a post having a notch and further comprises a ridge which engages the notch.

7. The test sample preparation device of claim 5 wherein the post is mounted to the housing and the ridge is mounted to the sampler tray.

8. The test sample preparation device of claim 4 wherein the key mechanism comprises a notch and a ridge which engages the notch.

9. The test sample preparation device of claim 1 wherein the key mechanism comprises a notch and a ridge which engages the notch.

10. The test sample preparation device of claim 9 wherein the notch is associated with the housing and the sampler tray has the ridge.

11. A test sample preparation device for simultaneously preparing multiple samples directly into vials coupled to a sampler tray, the device comprising:
   a housing having an opening, an interior and an exterior, the housing including a vacuum channel, the vacuum channel providing fluid communication between the interior and the exterior of the housing and being capable of coupling a vacuum source to the interior of the housing;
   filter assembly disposed over the opening of the housing, the filter assembly including a plurality of wells, each well having two open ends, and a plurality of porous media disposed in the wells, respectively;
   a sampler tray removably disposed in the housing;
   a plurality of vials removably coupled to the sampler tray, the vials being in liquid receiving relationship with the wells, respectively; and
   a key mechanism coupled to the housing to uniquely define the position of each vial with respect to the housing, wherein the key mechanism includes a post having first and second ends, an annular protrusion at the second end of the post, and a notch in the annular protrusion.

12. The test sample preparation device of claim 11 wherein the first end of the post is attached to the housing and the key mechanism further includes a ridge mounted to the sample tray and engaged with the notch.

* * * * *